US007772194B2

(12) United States Patent
Lowe et al.

(10) Patent No.: US 7,772,194 B2
(45) Date of Patent: Aug. 10, 2010

(54) PESTICIDAL FORMULATIONS

(75) Inventors: Lionel Barry Lowe, South Wales (AU);
James Terence Rothwell, South Wales (AU)

(73) Assignee: Eli Lilly and Company, Indianapolis, IN (US)

( * ) Notice: Subject to any disclaimer, the term of this patent is extended or adjusted under 35 U.S.C. 154(b) by 2 days.

(21) Appl. No.: 10/488,076

(22) PCT Filed: Sep. 17, 2001

(86) PCT No.: PCT/AU01/01169

§ 371 (c)(1),
(2), (4) Date: Sep. 28, 2004

(87) PCT Pub. No.: WO03/024223

PCT Pub. Date: Mar. 27, 2003

(65) Prior Publication Data
US 2005/0032716 A1 Feb. 10, 2005

(51) Int. Cl.
*A61K 31/70* (2006.01)
(52) U.S. Cl. .......................................... 514/27; 514/30
(58) Field of Classification Search .................. 514/27, 514/30
See application file for complete search history.

(56) References Cited

U.S. PATENT DOCUMENTS

| 4,740,432 | A | 4/1988 | Bosserelle |
| 4,927,813 | A | 5/1990 | Bernstein |
| 5,059,593 | A | 10/1991 | Stendel et al. |
| 5,145,684 | A | 9/1992 | Liversidge et al. |
| 5,202,242 | A | 4/1993 | Mynderse et al. |
| 5,227,163 | A | 7/1993 | Eini et al. |
| 5,227,295 | A | 7/1993 | Baker |
| 5,288,483 | A | 2/1994 | Cardin et al. |
| 5,362,634 | A | 11/1994 | Boeck et al. |
| 5,496,931 | A | 3/1996 | Boeck et al. |
| 5,496,932 | A | 3/1996 | McCurry, Jr. et al. |
| 5,539,089 | A | 7/1996 | Broughton et al. |
| 5,571,901 | A | 11/1996 | Boeck et al. |
| 5,591,606 | A | 1/1997 | Turner et al. |
| 5,631,155 | A | 5/1997 | Turner et al. |
| 5,670,364 | A | 9/1997 | Mynderse et al. |
| 5,670,486 | A | 9/1997 | Mynderse et al. |
| 5,767,253 | A | 6/1998 | Turner et al. |
| 5,840,861 | A | 11/1998 | Mynderse et al. |
| 5,880,076 | A | 3/1999 | Vermeer |
| 6,001,981 | A | 12/1999 | DeAmicis et al. |
| 6,010,710 | A | 1/2000 | Etchegaray et al. |
| 6,022,559 | A | 2/2000 | Simonnet |
| 6,063,771 | A | 5/2000 | Snyder |
| 6,096,326 | A | 8/2000 | Wikholm |
| 6,235,754 | B1 | 5/2001 | Watson et al. |
| 6,342,482 | B1 | 1/2002 | Snyder |
| 6,395,765 | B1 | 5/2002 | Etchegaray |
| 6,583,088 | B1 | 6/2003 | Andersch |
| 2003/0055089 | A1 | 3/2003 | Sirinyan et al. |

FOREIGN PATENT DOCUMENTS

| AU | 1999 49070 A1 | 7/1999 |
| AU | 49070/99 | 2/2000 |
| CA | 2059602 | 7/1992 |
| DE | 35 31 920 | 3/1987 |
| EP | 0 069 269 | 1/1983 |
| EP | 0 128 351 | 12/1984 |
| EP | 0 214 731 B1 | 7/1986 |
| EP | 0 285 176 B1 | 3/1988 |
| EP | 0 308 145 A2 | 9/1988 |
| EP | 0 475656 | 3/1992 |
| EP | 0 295 1177 B1 | 6/1996 |
| EP | 0 375 316 B1 | 12/1999 |
| EP | 0 968 706 | 1/2000 |
| GB | 2 088 212 | 6/1982 |
| GB | 2 135 886 | 9/1984 |
| GB | 2 317 564 | 4/1988 |
| WO | WO 82/02647 | 8/1982 |
| WO | WO 92/05764 | 4/1992 |
| WO | WO 93/09126 | 5/1993 |

(Continued)

OTHER PUBLICATIONS

DeAmicis, et al., "Physical and Biological Properties of the Spinosyn: Novel Macrolide Pest-Control Agents from Fermentation," Americal Chemical Society, Chapter 11, 144-154 (1997).
Winkle, et al., "Rheological Studies on Suspension Concentrates," Jun. 12, 1988; XP002153298; Online—http://www.chemsoc.org/chempest/html/2A-0024.html; abstract.
Spinosad Technical Guide.
Boech, et al., Chemical Abstracts, 114, 9, Abstract No. 80066m (1991).
Kirst, et al., "Discovery Isolation, and Structure Elucidation of a Family of Structurally Unique, Fermentation-Derived Tetracyclic Macrolides," ACS Symposium Series, Snythesis and Chemistry of Agrochemicals III, 504, pp. 214-225 (1992).
Crouse, et al., "Naturally Derived Materials as Products and Leads for Insect Control: The Spinosyns," Rev. Toxicol, 2, pp. 133-146 (1998).

(Continued)

*Primary Examiner*—Elli Peselev
(74) *Attorney, Agent, or Firm*—James J. Sales

(57) ABSTRACT

The present invention relates to an active composition for controlling or eradicating Phthiraptera, Siphonaptera and Acarina Pests, typically in domestic animals, comprising a synergistic combination of at least one A83543 compound and at least one macrocyclic lactone. The invention also relates to the use of the active composition in pesticidal formulations, the formulations themselves and to the various applications of those formulations as pesticides, specifically in controlling all species of Phthiraptera, Siphonaptera and Acarina pests, typically in domestic animals. Such applications include the control of such external Phthiraptera, Siphonaptera and Acarina pests in domestic animals including but not limited to sheep, cattle, poultry, pigs, goats, camelids, horses, dogs and cats.

14 Claims, No Drawings

FOREIGN PATENT DOCUMENTS

| WO | WO 94/20518 | 9/1993 |
|---|---|---|
| WO | WO 94/26113 | 11/1994 |
| WO | WO 97/00265 | 1/1997 |
| WO | WO 97/33471 | 9/1997 |
| WO | WO 98/03070 | 1/1998 |
| WO | WO 98/23158 | 6/1998 |
| WO | WO 00/01347 | 6/1999 |
| WO | WO 00/02453 | 1/2000 |
| WO | WO 00/29378 | 5/2000 |
| WO | WO 00/30449 | 6/2000 |
| WO | WO 00/60940 | 10/2000 |
| WO | WO 01/11961 | 2/2001 |
| WO | WO 01/11962 | 2/2001 |
| WO | WO 01/11963 | 2/2001 |
| WO | WO 01/11964 | 2/2001 |
| WO | WO 01/12156 | 2/2001 |
| WO | WO 01/19840 | 3/2001 |
| WO | WO 01/40446 | 6/2001 |
| WO | WO 01/70028 | 9/2001 |

OTHER PUBLICATIONS

Mertz, F. P., et al., "*Saccharopolyspora spinosad* sp. Nov. Isolated from Soil Collected in a Sugar Mill Rum Still," Int. J. System Bacteriol, 40, pp. 34-39 (1990).

Salgado, V. L., "Studies on the Mode of Action of Spinosad: Insect Symptoms and Physiological Correlates," Pestic. Biochem. Physiol., 60, pp. 91-102 (1998).

Thompson, G. D., et al., "Spinosad A Case Study: An Example from a Natural Products Discovery Programme," Pest. Manag. Sci., 56, pp. 696-702 (2000).

Thompson, G. D., "The Discovery of *Saccharopolyspora spinosad* and a New Class of Insect Control Products," Down to Earth, 52, pp. 1-5 (1997).

Breuninger, J. M., "Conserve SC: A New Product for the Turfgrass and Ornamental Industry," Down to Earth, 53, pp. 1-5 (1998).

Nolting, S. P., "Insect Control in Cotton with Tracer," Down to Earth, 52, pp. 21-27 (1997).

Sparks, et al., "Biological Activity of the Spinbsyns, New Fermentation Derived Insect Control Agents, on Tobaco Budworm (Lepidopters: Noctuidae) Larvae," J. Econ. Entomol., 91, pp. 1277-1283 (1996).

Kirst, et al., Tetrahydron Letters, 32(37), 4839-4842 (1991).

Snyder, et al., J. Am. Chem. Soc., 106, 787-789 (1984).

T. C. Sparks, et al., "Biological Characteristics of the Spinosyns: A New Naturally Derived Insect Control Agents," Cotton Insect Research and Control Conference, 1995 Beltwide Cotton Conferences, pp. 903-907.

G. D. Thompson, "Spinosyns: An Overview of New Natural Insect Management Systems," Cotton Insect Research and Control Conference, 1995 Beltwide Cotton Conferences, pp. 1039-1043.

*Agricultural Chemical News*, 195(2), "NAF-85 (spinosad): DowElanco insecticide" (1995).

*Agricultural Chemical News*, 186(2), "Spinosad, NAF-144; DowElanco seeks EPA approval for insecticide" (1995).

Spencer, et al., "Spinosad insect control agent; lack of effects in a one year neurotoxicity screening study in rats," Fundam. Appl. Tocicol.; Pt. 2, 211, 30(1) (1996).

Kirst, et al., "Chemistry of Biology of the spinosyns a new class of naturally derived insect control agents," *Abstracts of Papers Americal Chemical Society*; 210$^{th}$ American Chemical Society, 210, Part 1, Abstract No. AGRO061.

Adan, et al., "Laboratory evaluation of the novel naturally derived compound spinosad against ceratitis capitata," *Pesticide Science*, 48(3), pp. 261-268 (1996).

Boyd, Impact of insecticides on predators of the soybean looper, pseudoplusia inc, *PhD Dissertation*, The Louisiana State University and Agricultural and Mechanical Col., UMI(9637762).

King, et al., Spinosad bait for the Caribbean fruit fly (Kiptera: Tephritidea), *Florida Entomologist*, 79(4) pp. 526-531 (1996); ISSN: 0015-4040.

Magnussen, et al., "Characterization of spinosad related residues in poultry tissues and eggs following oral administration," 211$^{th}$ American Chemical Society National Meeting, New Orleans, Louisiana, USA, 211:1-2; AGRO 43; ISSN 0065-7 (1996).

Saunders, et al., "Degradation of spinosad in aqueous solution," *211$^{th}$ Americal Chemical Society National Meeting*, New Orleans, Louisiana, USA, 211, Part 1, Abstract No. AGRO048.

Sparks, et al., "Chemistry and biology of the spinosyns: components of spinosad (Tracer), the first entry into DowElanco's naturalyte class of insect control products," *Proc.—Beltwide Cotton Conf.*, 2:692-696 (1996); ISSN: 1059-2644.

Burton, et al., "Tracer naturalyte insect control physical property attributes," *Proc.—Beltwide Cotton Conf.*, 2:696-697 (1996); ISSN: 1059-2644.

Thompson, et al., "Spinosad and the new naturalyte insect control class," *Proc.—Beltwide Cotton Conf.*, 2:870-872 (1996); ISSN: 1059-2644.

Murray, et al., "The effects of spinosad (Tracer) on pests and beneficials," *Australian Cottongrower*, 18:62-64 (1997).

Heller, et al., "Evaluation of experimental DowElanco NAF85 and NAF127 formulations, and Dursban Pro for management of black cutworm on creeping bentgrass, 1996," *Anthropod Management Tests*, 22:345 (1997).

Heller, et al., "Evaluation of NAF formulations, Dursban Pro, and Scimitar CS for management of black cutworm on creeping bentgrass, 1995," *Arthropod Management Tests*, 22:346 (1997).

Salgado, et al., "Studies on the mode of action of spinosad, the active ingredient in Tracer insect control," *Proc.—Beltwide Cotton Conference*, 2:1082-1084 (1997); ISSN: 1059-2644.

Murrey, et al., "The effect of spinosad (Tracer) on arthropod pest and beneficial populations in Australian cotton," *Proc.—Beltwide Cotton Conf.*, 2:1087-1091 (1997); ISSN: 1059-2644.

Sparks, et al., "Penetration and metabolism of spinosyn A in lepidopterous larvae," *Proc.—Beltwide Cotton Conference*, 2:1259-1264 (1997); ISSN: 1059-2644.

*Agricultural Chemical News*, "Success (spinosad): a new DowElanco insecticide formulation," 209: pp. 2-15 (1997).

*Agricultural Chemical News*, "Tracer (spinosad): DowElanco gains insecticide registration," 211; pp. 3-15 (1997).

*Agricultural Chemical News*, "Success (spinosad): DowElanco gains 24(c) insecticide label to use in California," 213; pp. 2-15 (1997).

*Agricultural Chemical News*, "Conserve SC (spinosad): DowElanco gains EPA, USA, insecticide registration," 215; pp. 1-15 (1997).

Yeh, et al., "Application of empore disc extraction for trace analysis of spinosad and metabolites in leafy vegetables, pepper, and tomatoes by high-performance liquid chromatography with ultraviolet detection," *Journal of Agricultural and Food Chemistry*, vol. 45, No. 5, pp. 1746-1751; ISSN 0021-8561.

Boyd, et al., "Residual toxicity of selected insecticides to heteropteran predaceous species (Heteroptera: Lygaeidae, Nabidae, Pentatomidae) on soybean," *Environ. Entomol.*, vol. 27, No. 1, pp. 154-160 (1998).

Kolarid, et al., "Colorado potato beetle control, 1997," *Arthropod Management Tests*, vol. 23; pp. 124-126 (1998).

Cowles, "Effect of spinosad formulations and other miticides on twospotted spider mite, 1995," *Arthropod Management Tests*, vol. 23; pp. 342-343 (1998).

Kjaer, et al., "The impact of phenology, exposure and instar susceptibility on indecticide effects on a chrysomelid beetle population," *Prestic. Sci.*, vol. 52, No. 4, pp. 361-371 (1998).

Marty, et al., "The maternal and developmental toxicity of spinosad in Sprague-dawley rats and New Zealand White rabbits," *Teratology*, vol. 57, pp. 4-5 (1998).

Salgado, et al., "Studies on the mode of action of spinosad: The internal effective concentration dependence of neural excitation," *Pesticide Biochemistry and Physiology*, vol. 60, No. 2, pp. 103-110 (1998).

Boyd, et al., "Susceptibility of predaceous hemipteran species to selected insecticides on soybean in Louisiana," *Journal of Economic Entomology*, vol. 91, No. 2, pp. 401-409 (1998).

Woodburn, et al., "Bioconcentration and metabolism of a unique insecticide (spinosyn) by the Rainbow trout," *Second World Congress of the Society of environmental toxicology and chemi*,PT127; pp. 5-9 (1995).

Stoltz, et al., "Colorado potato beetle control with foliar sprays, 1995," *Arthropod Management Tests*, vol. 21, pp. 168-169.

Sewell, et al., "Irish potato, control of Colorado potato beetle, 1995," *Arthropod Management Tests*, vol. 21, pp. 158-159.

Olson, et al., "Potato, Colorado potato beetle control with spinosad, 1995," *Arthropod Management Tests*, vol. 21; pp. 154-155.

Noetzel, et al., "Control of resistant Colorado potato beetle, Blaine, MN, 1995," *Arthropod Management Tests*, vol. 21, p. 149.

Noetzel, et al., "Colorado potato beetle control, Crookston, MN, 1995," *Arthropod Management Tests*, vol. 21, pp. 145-146.

Hedin, et al., "Physical and biological properties of the spinosyns: novel macrolide pest-control agents from fermentation," Phytochemicals for Pest Control, Chapter 11, 1995 *International Chemical Congress of Pacific Basin Societies;* ACS Symposium Series 658, pp. 144-153.

Boyd, "Impact of insecticides on predators of the soybean looper, Pseudoplusia inc, "*Dissertation;* UMI(9637762):[97pp]; The Louisiana State University and Agriculture.

Sears, et al., "Effects of various rates and combinations of insecticides on the control of Colorado potato beetle (CPB)(1995) " *Pest Management Research Report—Insects and Diseases,* ICAR: 86100104; pp. 159-161; Report No. 061 (1995).

J. M. Edwards, et al., "Potential of Spinosad as a Control Agent for Diptera," ESA Annual Meeting, Las Vegas, Nevada, Dec. 17-21 (1995).

D. P. Rainey, et al., "The tissue distribution and metabolism of spinosyn A and D lactating goats," XP002153173 (found from STN-International Association accession No. 1996-85 398 CROPU & Abstr. Pap. Am. Chem. Soc. (211 MEET, Pt. 1, AGR0045, 1996).

D. H. Da, et al., Dermal absorption and metabolism of spinosad in lactating goats, Accession No. PREV199900165412; XP002153532.

DeAmics, et al., ACS Sympos. Ser. 658,144-154 (1997), CA 126: 234728.

Database WPI, Week 198721, Derwent Publications Ltd., London, GB; AN 1987-145349; XP002153469 & HU 41 238 A (Nehezvegyipari), Apr. 28, 1987 abstract.

Chemical Abstracts, vol. 102, No. 3, Jan. 21, 1985 Columbus, Ohio, US; abstract No. 19640, Kieran, Peter John, et al: "Pour-on formulation for lice control" XP002153466 abstract & AU 83219 47 A (Wellcome Australia Ltd.) Apr. 12, 1984.

Chemical Abstracts, vol. 101, No. 11, Sep. 10, 1984 Columbus, Ohio, US; abstract No. 85712, Kieran, Peter John, et al.: "Pyrethroids for combating sheep ectoparasites" XP002153467 abstract & AU 82918 50 A (Wellcome Austalia Ltd.) Mar. 24, 1983.

Chemical Abstracts, vol. 100, No. 7, Feb. 12, 1984 Columbus, Ohio, US; abstract No. 47094, Kieran, Peter John et al.: "Control of sheep lice" XP002153468 abstract & AU 81770 04 A (Wellcome Australia Ltd.) May 27, 1982.

Kameoka, et al, "A Cutaneous Agranular CD2- CD4+ CD56+ Lymphoma", Am J. Clin. Pathol, 110, pp. 478-488 (1998).

Petrella, et al., "CD4+ CD56+ Cutaneous Neoplasms: A Distinct Hemotological Entity?" The American Journal of Surgical Pathology, 23(2), pp. 137-146 (1999).

Adachi, et al., High Expression of CD56 (N-CAM) in a Patient With Cutaneous CD4-Positive Lymphoma, American Journal of Hematology, 47, pp. 278-282 (1994).

Galibert, et al, "A Granular CD4+ CD56+ Hematodermic Neoplasm Originates from a Population of CD56+ Precursor Cells Related to Plasmacytoid Monocytes," XP000995064.

"Do Primary Cutaneous Non-T Non-B CD4+ CD56+ Lymphomas Belong to the Myelo-Monocytic Lineage?" XP000984547.

Derwent Abstract, 1991, 373544, abstract of JP 03251520A—Composition for shampoo.

Sabatini, G.A., et al.: *Tests to determine $LC_{50}$ and Discriminating Doses for Macrocyclic Lactones Against the Cattle Tick, Boophilus Microplus;* Veterinary Parsitology; 95 (2001), pp. 53-62.

Wade, Susan E., et al.: *Survival and Reproductuon of Artificially Fe Cat Fleas, Ctenocephalides Felis Bouché (Siphonaptera: Pulicidae)*; Department of Veterinary Microbiology, Immunology, and Parasitology, New York State College of Veterinary Medicine; May 1988, pp. 186-190.

El-Gazzar, L.M., et al.: *Insect Growth Regulators: Mode of Action on the Cat Flea, Ctenocephalides Felis (Siphonaptera: Pulicidae)*; J. Med. Entomol., vol. 23, No. 6, Dec. 1986, pp. 651-654.

Sun, Yun-Pei, et al.: *Analysis of Joint Action of Insecticides Against House Flies;* Journal of Economic Entomology; vol. 53, No. 5, Oct. 1960, pp. 887-892.

DeAmicis, Carl V., et al.: *Physical and Biological Properties of the Spinosyns: Novel Macrolide Pest-Control Agents from Fermentation;* ACS Symposium Series, ISSN 0097-6156; 658; Phytochemicals for Pest Control, Chapter 11, pp. 145-154.

D. Rugg, et al.: *A Laboratory Assay for Assessing the Susceptibility of Damalinia Ovis (Schrank) (Phthirapter: Trichodectidae) to Avermectins;* J. Aust. Ent. Soc., 32 (1993), pp. 1-3.

PESTICIDAL FORMULATIONS

This application claims priority to PCT/AU01/01169.

TECHNICAL FIELD

The present invention relates to combinations of pesticidally active compounds suitable for use as active agents in pesticidal formulations, the formulations themselves and to the various applications of those formulations as pesticides, specifically in controlling all species of Phthiraptera, Siphonaptera and Acarina pests. Such applications include the control of such external Phthiraptera, Siphonaptera and Acarina pests in domestic animals including but not limited to sheep, cattle, poultry, pigs, goats, camelids, horses, dogs and cats, as well as the household and rural applications of such formulations in control of such pests.

BACKGROUND OF THE INVENTION

Historically, the greatest damage to domestic animals and crops has been caused and continues to be caused by pests such as insects, fungi, nematodes and microbes. Insects particularly represent a cause for concern as they are the most numerous of all living organisms and constitute approximately 72% of all animal species. Approximately 1% of insects are considered pests in that they attack humans and/or domestic animals, transmit human, animal and plant diseases, destroy crops, objects and structures and compete for food and other necessities. It is estimated that enormous agricultural losses result worldwide from insect presence.

Domestic animals which include animals of agricultural worth such as sheep, cattle, horses, goats, pigs and other ruminants and monogastrics are almost invariably subject to the activity of pests including insects, acarides, acarina, siphonaptera, phthiraptera, anoplura and mallophaga. External parasites such as ticks, lice and fleas irritate the animals and can cause economic loss in the form of poor quality hide, wool or sheep skin, poor quality meat/tissue, reduced weight gain and even death as a result of the animal carrying harmful parasites.

The losses resulting from insect caused human and animal diseases are also enormous. In fact, insects are considered to be the carriers of more than 250 viruses which are pathogens of humans and higher animals. The numbers of human deaths caused by mosquito transmitted diseases such as malaria and lymphatic filariasis are huge. Flies also transmit human and animal related diseases such as trachoma, trypanosomiasis and river blindness.

However, out of the nearly one million species of arthropods which includes lice, ticks, flies and mites, only a small percentage require the application of control measures. To date, the primary method for controlling insects and other pests, particularly in respect of domestic animals (such as sheep, cattle, goats, horses and hogs) has been by the application of synthetic chemical pesticide compositions. It is estimated that there are at least 35,000 formulated pesticide products worldwide with chemicals as the active ingredients. Such pesticide products include antimicrobials, larvicides, insecticides, animal dips, avicides and disinfectants.

The extensive use of chemical insecticides since the 1940s has resulted in a large number of problems including widespread insect resistance, emergence of secondary pests, hazards to human and animal health as well as detrimental effects on fish and birds, environmental pollution and the increasing economic costs of new insecticides.

Many insect species have developed resistance to the action of specific insecticides so as to necessitate changes in control practices. There is an ever-widening pool of insect pests which are developing multiple resistance. The resistance genes having lengthy persistence in insect genomes which preclude successful reuse of an insecticide to control an insect population with resistant genes.

Pesticide/insecticide residues and their consequential many potential human, animal and environmental risks are also seen as one of the major problems resulting from chemical usage, particularly those formulations containing active agents which include organophosphates or synthetic pyrethroids. With the exception of microbial insecticides, nearly all pesticides result in residues of various chemicals and their degradation products or metabolites which may be present in detectable amounts (ppb to ppm) in food despite food processing. Tissue/meat residues are also a major concern when considering use of insecticides on farm animals.

Potential human risks from the use of such insecticides include acute toxic reactions to the insecticide such as poisoning, skin and eye irritations, as well as possible long term effects such as cancer, birth defects, and reproductive disorders. Acute inhalation toxicity as well as dermal penetration are also potential risks. Health hazards in humans may also arise from repeated exposure to a chemical over a limited period of time.

In particular, the currently used actives of synthetic pyrethroids and organophosphates which are commonly used in insecticidal formulations to control lice and flies, particularly on sheep, are not only toxic to animals but also to the human operator who applies them. Exposure in farmers or operators who handle both pesticide concentrates and the larger volumes of pesticide diluted for use, is a cause for concern. Further, it is possible for the operator to ingest pesticides not only by mouth, but also by breathing (eg spray drift) and by absorption through the skin (accidental spillage). Of particular concern has been the use of organophosphates where accidental exposure causes acute and chronic poisoning affecting the nervous system.

Accordingly, insect and other pest control has been sought to be directed away from exclusive reliance on insecticides and towards the optimisation of environmental and economic insect and pest control (integrated pest management). The application of microbial control in which insects are attacked by pathogens such as viruses, bacteria, fungi and protozoa are favoured as such microbial insecticides are highly selective for insect pests and do not leave toxic residues. However, such microbial insecticides are not without their problems such as the difficulty in applying as well as confining the natural enemy/parasite/disease to a large area. Further, they also have the disadvantage of short residual action and extreme specificity which limits general applicability.

Biological control has been recently applied in the area of insecticides/pesticides through the release of sterilised male insects. Genetic engineering has also recently been applied by way of mass introduction of deleterious mutations such as chromosomal translocations. However, such procedures are very expensive and stringent criteria are required before release of sterile males is contemplated. Chemosterilants which sterilise large segments of insect pest populations are also known but are strong carcinogens which precludes their use.

The use of chemical insecticides and pesticides and their environmental and economic viability, the dangerous nature and magnitude of the persisting residues as well as increasing insect and pest resistance, together with high toxicity levels of many chemical insecticides, has resulted in the search for new substances or approaches to insect and other pest control.

There is therefore a need for compounds and combinations thereof which can be used as active agents in pesticides, particularly against insects which afflict domestic animals or their environs, and which are effective at low application rates, selective in biologic action and have low toxicity and a high margin of safety to humans, crops, economic animals, aquatic organisms and birds. Such compounds and combinations must be both environmentally friendly in that there must be demonstrably low impacts on the environment, as well as economically viable to use on a large scale. Further, there must be none or little insect or other pest resistance to such compounds or combinations. Fermentation product A83543, also known as spinosyn, includes a family of related compounds (spinosyns) produced by *Saccharopolyspora spinosa*. These are naturally derived fermentation products with a positive safety profile in contrast to currently used synthetic organically derived compounds (such as synthetic pyrethroids, organophosphates, organochlorines and carbamates), and have previously been shown to exhibit excellent insecticidal activity. Accordingly by the term "A83543 compounds" which has the same scope as the phrase "spinosyn and derivatives and analogues thereof" is meant components consisting of a 5,6,5-tricyclic ring system, fused to a 12-membered macrocyclic lactone, a neutral sugar (2N,3N,4N-tri-O-methylrhamnose) and an amino sugar (forosamine). The family of natural components of A83543 include a genus taught in EPO patent application No. 0375316 and having the following general formula:

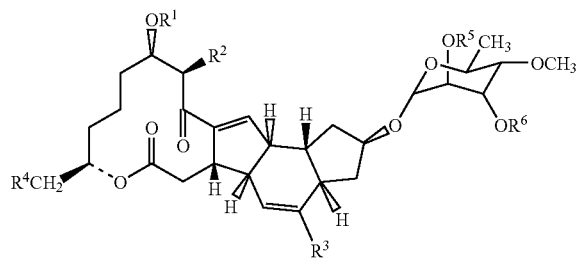

wherein $R^1$ is H or a group selected from

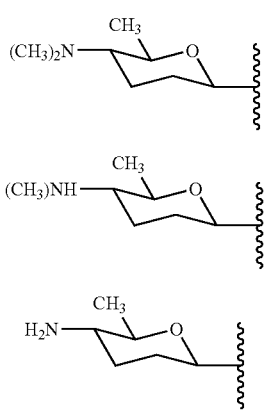

-continued

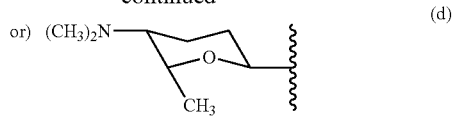

and $R^2$, $R^4$, $R^3$, $R^5$ and $R^6$ are hydrogen or methyl; or an acid addition salt thereof when $R^1$ is other than hydrogen.

The family of compounds from A83543 fermentation product has been shown to comprise individual compounds A83543A, A83453B, A83543C, A83453D, A83543E, A83453F, A83543G, A83453H, A83543J, A83453L, A83543M, A83453N, A83543Q, A83453R, A83543S, A83453T, A83453U, A83543V, A83453W, A83453X. Boeck et al. described spinosyns A-H and J and salts thereof in U.S. Pat. Nos. 5,362,634, 5,496,932 and 5,571,901 which are incorporated herein by reference. Mynderse et al. described spinosyns L-N, their N-demethyl derivatives and salts thereof in U.S. Pat. No. 5,202,242 incorporated herein by reference. Turner et al. described spinosyns Q-T, their N-demethyl derivatives and salts thereof in U.S. Pat. Nos. 5,591,606, 5,631,155 and 5,767,253 which are also incorporated herein by reference. Spinosyns K,O,P,U,V,W, and Y are described in the article by DeAmicis, C. V. et al. in American Chemical Society's Symposium Series: Phytochemicals for Pest Control (1997), Chapter 11 "Physical and Biological Properties of Spinosyns: Novel Macrolide Pest-Control Agents from Fermentation" pp 146-154.

Spinosyn A (A83543A) was the first spinosyn isolated and identified from the fermentation broth of *Saccharapolyspora spinosa*. Subsequent examination of the fermentation broth revealed that the parent strain of *S. spinosa* produced a number of spinosyns (A83543A to J). Compared to spinosyn A, spinosyns B to J are characterised by differences in the substitution patterns on the amino group of the forosamine, at selected sites on the ring system and on the neutral sugar. The strains of *S. spinosa* produce a mixture of spinosyns which primary components are spinosyn A (~85%) and spinosyn D (~15%). These are the two spinosyns that are currently known as the most active as insecticides.

Similar to the spinosyns, macrocyclic lactones have also previously been shown to exhibit excellent insecticidal activity. Macrocyclic lactones have a complex ring structure and include such well known anthelmintic compounds as avermectins and milbemycins. The avermectins are isolated from fermentation products of *Streptomyces avermitilis* and ivermectin is a compound which is a semisynthetic chemical formed by modification of avermectin. The basic structure of the avermectins is a 16-membered lactone ring to which are appended three main substituent groups: a hexahydrobenzofuran group, a disaccharide group (at C-13) and a spiroketal ring (C-17 to C-28). Doramectin is a novel avermectin. Milbemycins are other compounds which are not avermectins but which can be considered to come within the class of compounds which are macrocyclic lactones. The milbemycins differ structurally from the avermectin group, mainly in the absence of a disaccharide group on C-13. Milbemycin D and milbemycin 5-oxime are two such macrocyclic lactones. Moxidectin is derived from the fermentation product nemadectin and possesses a methoxime substituent on C-23.

The present invention resides in the discovery of a synergistic combination of pesticidal compounds, the formulation and application of specific pesticidally active agents based on the synergistic combination and their use in pesticidal formulations against Phthiraptera, Siphonaptera and Acarina pests, particularly in domestic animals.

OBJECTS OF THE INVENTION

Accordingly, it is an object of this invention to provide a pesticidal composition which is systemically active against Phthiraptera, Siphonaptera and Acarina pests, containing a synergistic combination of at least one A83543 compound and at least one macrocyclic lactone.

It is also an object of this invention to provide a pesticidal composition which is systemically active against Phthiraptera, Siphonaptera and Acarina pests in domestic animals including cattle, camelids, pigs, dogs, horses, cats, sheep, goats and poultry, containing a synergistic combination of at least one A83543 compound and at least one macrocyclic lactone.

It is another object of this invention to provide one or more pesticidal formulations systemically active against Phthiraptera, Siphonaptera and Acarina pests, containing a synergistic combination of at least one A83543 compound and at least one macrocyclic lactone as the active principles together with at least one acceptable carrier or diluent.

It is another object of this invention to provide one or more pesticidal formulations systemically active against Phthiraptera, Siphonaptera and Acarina pests in domestic animals including cattle, camelids, pigs, horses, dogs, cats, sheep, goats and poultry, containing a synergistic combination of at least one A83543 compound and at least one macrocyclic lactone as the active principles together with at least one acceptable carrier or diluent.

It is also an object of the present invention to provide a method of eliminating and/or controlling Phthiraptera, Siphonaptera and Acarina pests in domestic animals including cattle, camelids, pigs, horses, dogs, cats, sheep, goats and poultry by applying or administering to said animals a pesticidally active combination of compounds alone or together with an acceptable carrier or diluent, such that said pesticidally active combination is systemically delivered to said Phthiraptera, Siphonaptera and Acarina pests.

It is also an object of the present invention to provide a method of eliminating and/or controlling Phthiraptera, Siphonaptera and Acarina pests by administering to said pests a pesticidally active combination of compounds alone or together with an acceptable carrier or diluent, such that said combination is present systemically in said pests.

The term 'Phthiraptera' or 'Phthiraptera pests' as used herein defines members of the insect order Phthiraptera, which are parasitic during one or more stages of their life cycle, including the immature stage (which is defined to include larval (nymph) forms), the adult stage or both stages and further includes Phthiraptera insect eggs.

The term 'Siphonaptera' or 'Siphonaptera pests' as used herein defines members of the insect order Siphonaptera which are parasitic during one or more stages of their life cycle, including the immature stage (which is defined to include larval forms), the adult stage or both stages and further includes Siphonaptera insect eggs.

The term 'Acarina' or 'Acarina pests' as used herein defines members of the Arachnida order Acarina which are parasitic during one or more stages of their life cycle, including the immature stage (which is defined to include larval (nymph) forms), the adult stage or both stages and further includes Acarina eggs.

It is further noted that for the purposes of the present application, the term 'spinosyn or analogue or derivative thereof' is defined to include an individual spinosyn factor (A83543A-H, J-W or Y) an N-demethyl or other derivative of an individual spinosyn factor, or salt thereof, or a combination thereof, consistent with the disclosure of the abovementioned references which have been incorporated herein. As stated above, the term "A83543 compound" is used herein to mean an individual spinosyn factor, or an analogue, a derivative or salt thereof, or a combination thereof.

The term 'controlling or eradicating' is used to refer to a decrease in the number of living insects or arachnids (adult or immature forms) or to a decrease in the number of viable insect or arachnid eggs. The extent of reduction somewhat depends on the application rate and the active used.

The term 'effective amount' also used herein means the amount which is sufficient to cause a measurable reduction in the treated insect or arachnid population.

The word 'carrier' is used throughout the present specification to include carrier blends, that is mixtures of more than one substance.

The term 'synergistic' as used herein is defined to mean a combination of components wherein the activity of the combination is greater than the additive of the individual activities of each component of the combination.

The term 'macrocyclic lactone' as used herein is defined to be compounds of the classes of milbemycins and avermectins, including both naturally occurring compounds and synthetic derivatives thereof, especially those mentioned herein and in the art cited herein.

The term 'domestic animal' as used herein is defined to include animals of agricultural worth and companion animals, including but not limited to cattle, camelids, pigs, dogs, cats, sheep, poultry, horses and goats a well as other ruminants and monogastrics.

The term 'systemically active' as used herein is defined to mean having an effect or efficacy only when present within the system of a pest, such as after ingestion or other administration which results in a systemic presence of an active in a pest. The term does not mean having an effect or efficacy when present with the system of a host domestic animal, it is limited to activity or efficacy when systemically present within a pest.

SUMMARY OF THE INVENTION

A first aspect of the present invention provides an active composition for controlling or eradicating Phthiraptera, Siphonaptera and Acarina pests, said composition being systemically active in said pests and comprising a synergistic combination of at least one A83543 compound and at least one compound which is a macrocyclic lactone. A second aspect of the present invention provides a formulation for controlling or eradicating Phthiraptera, Siphonaptera and Acarina pests in domestic animals, said formulation including an effective amount of a systemically active composition of the first aspect of the invention and an acceptable carrier, diluent or excipient.

A third aspect of the present invention provides an externally applied formulation for control or eradication of Phthiraptera, Siphonaptera and Acarina pests in domestic animals, said formulation including an effective amount of a systemically active composition of the first aspect of the invention and an acceptable carrier.

A fourth aspect of the present invention provides a pesticidal bait formulation for control or eradication of Phthiraptera, Siphonaptera and Acarina pests, said formulation including an effective amount of a systemically active composition of the first aspect of the invention and an acceptable carrier.

A fifth aspect of the present invention provides an orally administered formulation for control or eradication of Phthiraptera, Siphonaptera and Acarina pests in domestic animals, said formulation including an effective amount of a systemically active composition of the first aspect of the invention and an acceptable carrier, diluent or excipient.

A sixth aspect of the present invention provides a parenterally administered formulation for control or eradication of Phthiraptera, Siphonaptera and Acarina pests in domestic animals, said formulation including an effective amount of a systemically active composition of the first aspect of the invention and an acceptable carrier, diluent or excipient.

A seventh aspect of the present invention provides a method of controlling or eradicating Phthiraptera, Siphonaptera and Acarina pests in domestic animals, said method including the external application of an effective amount of a systemically active composition according to the first aspect of the invention, or of a formulation according to the second or third aspects of the invention to a localised area of the external surface of said animal.

An eighth aspect of the present invention provides a method of controlling or eradicating Phthiraptera, Siphonaptera and Acarina pests, said method including the administration of an effective amount of a systemically active composition according to the first aspect of the present invention, or of a formulation according to the second or fourth aspects of the invention directly to said pests.

A ninth aspect of the present invention provides a method of controlling or eradicating Phthiraptera, Siphonaptera and Acarina pests in domestic animals, said method including the oral administration of an effective amount of a systemically active composition according to the first aspect of the invention, or of a formulation according to the second or fifth aspects of the invention to said animals.

A tenth aspect of the present invention provides a method of controlling or eradicating Phthiraptera, Siphonaptera and Acarina pests in domestic animals, said method including the parenteral administration of an effective amount of a systemically active composition according to the first aspect of the invention, or of a formulation according to the second or sixth aspects of the invention to said animals.

An eleventh aspect of the present invention provides the use of a systemically active composition of the first aspect of the present invention in the manufacture of a medicament for controlling or eradicating Phthiraptera, Siphonaptera and Acarina pests in domestic animals.

A twelfth aspect of the present invention provides the use of a systemically active composition of the first aspect of the present invention in the manufacture of a bait formulation for controlling or eradicating Phthiraptera, Siphonaptera and Acarina pests. Another aspect of the present invention provides an active composition of the first aspect of the present invention or a formulation of any one of the second to sixth aspects of the present invention when used for controlling or eliminating Phthiraptera, Siphonaptera and Acarina pests in domestic animals.

A further aspect of the present invention provides an active composition of the first aspect of the present invention or a formulation of the fourth aspect of the present invention when used for controlling or eliminating Phthiraptera, Siphonaptera and Acarina pests.

This invention is predicated upon the surprising discovery of a synergistic interaction between spinosyns and macrocyclic lactones. Whilst not wishing to be bound by theory, it is noted that macrocyclic lactones have a primary effect on the insect nervous system by activating inhibitory glutamate receptors, while spinosyns primarily activate the nicotinic acetylcholine receptors in insect neurones causing hyperactivity of neurones. However, both spinosyns and macrocyclic lactones have a secondary effect on gamma aminobutyric acid (GABA) gated chloride channels in arthropod neurones, GABA being an inhibitory neuro-transmitter. It is therefore possible that when combined together the spinosyns and macrocyclic lactones have a synergistic effect on the GABA receptor leading to effects in an insect's nervous system, this being unrelated to the primary effect of either spinosyns or macrocyclic lactones.

In particular, in the present invention it is surprisingly demonstrated that synergism occurs when a spinosyn and a macrocyclic lactone are delivered together to Phthiraptera, Siphonaptera or Acarina animal pests in such a way that those chemicals are ingested or are otherwise present systemically in the pests. Surprisingly, this effect is not observed in in vitro assays which rely on contact such as treated paper or transient immersion in treated solutions. While not wishing to be bound by theory, it is speculated that this difference is related to the mechanisms of action and the nature of both chemicals which have low vapour pressure and do not readily cross the cuticle of arthropods.

Typically, the first aspect of the present invention provides an active composition for control or eradication of Phthiraptera, Siphonaptera and Acarina pests, typically in domestic animals, said composition being systemically active in said pests and being a synergistic combination of a spinosyn and a macrocyclic lactone compound, wherein the spinosyn:macrocyclic lactone compounds are present in the range of 1000:1 to 1:1000 w/w. In particular, the ratio of ivermectin:spinosad could be 1:1000 in a composition systemically active in heartworm (*Dirofilaria immitis*) or fleas.

It is however observed that the synergism also operates at lower ratios. Accordingly, typically, in the systemically active composition of the invention, the spinosyn compound:macrocyclic lactone compound are present in the range of 100:1 to 1:100 w/w.

Also typically, in the systemically active composition of the invention, the spinosyn compound:macrocyclic lactone compound are present in the range of 10:1 to 1:10 w/w.

Further typically, in the systemically active composition of the invention, the spinosyn compound:macrocyclic lactone compound are present in the range of 9:1 to 1:9 w/w.

More typically, in the systemically active composition of the invention, the spinosyn compound:macrocyclic lactone compound are present in the range of 8:1 to 1:8 w/w.

Also typically, in the systemically active composition of the invention, the spinosyn compound:macrocyclic lactone compound are present in the range of 7:1 to 1:7 w/w.

Also typically, in the systemically active composition of the invention, the spinosyn compound:macrocyclic lactone compound are present in the range of 6:1 to 1:6 w/w.

More typically, in the systemically active composition of the invention, the spinosyn compound:macrocyclic lactone compound are present in the range of 5:1 to 1:5 w/w.

Even more typically, in the systemically active composition of the invention, the spinosyn compound:macrocyclic lactone compound are present in the range of 4:1 to 1:4 w/w.

Most typically, in the systemically active composition of the invention, the spinosyn compound:macrocyclic lactone compound are present in the range of 3:1 to 1:3 w/w.

Also most typically, in the systemically active composition of the invention, the spinosyn compound:macrocyclic lactone compound are present in the range of 2:1 to 1:2 w/w.

Also most typically, in the systemically active composition of the invention, the spinosyn compound:macrocyclic lactone compound are present in the proportion of 1:1 w/w.

One embodiment of the first aspect of the present invention provides a systemically active composition being a synergistic combination of spinosad and an avermectin.

Typically, the macrocyclic lactone of the first aspect of the invention is selected from the group consisting of ivermectin (22,23-dihydroavermectin $B_1$ described in EP 295117), abamectin, avermectin $A_{1a}$, avermectin $A_{1b}$, avermectin $A_{2a}$, avermectin $A_{2b}$, avermectin $B_{1a}$, avermectin $B_{1b}$, avermectin $B_{2a}$, and avermectin $B_{2b}$. Also typically, the macrocyclic lactone of the first aspect of the invention can be selected from the group of compounds related to the naturally occurring avermectins above but which have a group at the 25-substituent other than the isopropyl or (S)-sec-butyl groups, as set out in European patent applications 0214731, 0284176, 0308145, 0317148, 0335541 and 0340832 Also typically, the macrocyclic lactone of the first aspect of the invention can include moxidectin (and derivatives disclosed in EP 259779A), doramectin and its analogues (described in EP0214731B), selamectin, eprinomectin, milbemycin including milbemycin oxime, milbemycin D (Antiobiotic B41D) and its analogues (described in U.S. Pat. No. 3,950,360) and nemadectins (described in EP 170006A).

More typically, the macrocyclic lactone of the first aspect of the invention is selected from the group consisting of ivermectin, moxidectin, doramectin, selamectin, milbemycin oxime, Milbemycin D, eprinomectin and abamectin.

Even more typically, the macrocyclic lactone of the first aspect of the invention is ivermectin.

More typically, the active composition is therefore a synergistic combination of spinosad and ivermectin which is systemically active in Phthiraptera, Siphonaptera and Acarina pests.

Typically in the formulations of the present invention, the carrier can be non-aqueous or aqueous and the active composition is suspended, dissolved or dispersed in the carrier. Also typically, the active composition can be admixed with a pharmaceutically or veterinarily acceptable diluent or carrier which is selected with regard to the intended route of administration and in accordance with standard practice In one embodiment, the carriers or excipients used in the formulations of the third and fourth aspects of the present invention include dust carriers, solvents, emulsifiers, wetting and dispersing agents and water. In particular, in the bait formulations of the fourth aspect of the present invention, the carriers or excipients include a food source such as blood or other tissue extracts and typically further include one or more of yeast, sugar, pheromones, flavours, scents, solvents, wetting and dispersing agents.

In another embodiment, the carriers or excipients used in the orally delivered formulations of the fifth aspect of the present invention include tabletting excipients such as starch or lactose, capsule excipients or carriers and excipients commonly used in solutions or suspensions including water, flavouring and colouring agents. Selection of the carrier is of course made on the basis of compatibility with the active composition, including such considerations as pH, moisture content and stability. Selection of the carrier is also made depending on the mode of application of the formulation—such as whether it is to be applied topically to a domestic animal or, or orally or parenterally adminstered to a domestic animal, or is instead to be administered directly, such as via a bait to the Phthiraptera, Siphonaptera or Acarina pests.

One embodiment of any one of the second to sixth aspects of the invention provides a formulation for controlling or eradicating Phthiraptera, Siphonaptera and Acarina pests, said formulation including:

(a) from 0.1 to 40% by weight of an active composition of the first aspect of the present invention, and (b) from 60-99.9% by weight of a suitable carrier.

Typically each dose of a formulation of the invention would contain 30 μg-2 g of each of the spinosyn compound and macrocyclic lactone compound, more typically a formulation would contain 1 mg-1 g of each of the spinosyn compound and macrocyclic lactone compound.

Formulations of the third aspect of the present invention are typically liquids and can be made up as concentrates and then diluted prior to use.

Formulations of the fourth aspect of the present invention being bait formulations are typically solids including powders, granular or dessicated forms. It is also typical that such bait formulations can be in the form of liquids or pastes.

It has long been common practice to control external parasites on sheep, cattle and other domestic animals including but not limited to goats, pigs and horses by the localised topical application of a formulation containing an active insecticide/parasiticide and a carrier/vehicle. Typically therefore, a formulation of the third aspect of the invention is a pour-on formulation including an effective amount of an active composition of the first aspect of the invention and a topically acceptable carrier.

It is also typical that a topically applied formulation can be a spray or dip or a solution such as a jetting fluid.

A pour-on formulation of the third aspect of the present invention is typically liquid and is usually applied to the exterior of a domestic animal as a line or a spot, which when ingested by such Phthiraptera, Siphonaptera and Acarina pests, for example after feeding on a treated domestic animal epidermis, acts systemically in those pests thereby protecting the animal against both immature and adult forms of Phthiraptera, Siphonaptera and Acarina pests such as ticks, fleas and lice and can also act to decrease the number of viable Phthiraptera, Siphonaptera and Acarina eggs.

While the formulation is applied topically, to a localised area, the active agent migrates over the surface of the animal to cover its whole external surface area.

The carrier (also referred to herein as 'vehicle') present in such pour-on formulations of the third aspect of the present invention is formulated to achieve good spread around the skin and/or penetration of the epidermis of the animal. To date, commercial pour-on formulations are suspensions, emulsifiable concentrates or solutions and are often comprised of at least one organic solvent. Solvents commonly used as carriers in such pour-on formulations include propylene glycol, paraffins, isoparaffins, aromatics, isopropylmyristate (IPM), glycol ethers, alcohols and n-propyl alcohol.

It is important to note that the topical formulations of the present invention can be used to control the arthropods of the orders Phthiraptera, Siphonaptera and Acarina in several ways. In respect of topical formulations of the present invention which just purely remain on the external surface of a domestic animal, these will be effective against pests such as biting lice and other pests which feed off the epidermis of the animal and will thereby ingest the systemically active formulations. In respect of topical formulations of the present invention which after being topically applied at least partially penetrate through the epidermis of a domestic animal, penetrating into the extracellular fluid and then draining via the lymphatic system of the animal into its blood stream, these formulations will be effective against blood sucking pests such as fleas, ticks and some lice. These pests will be specifically killed if they ingest blood containing the systemically active composition of the present invention. Accordingly, topical formulations of the present invention can also become (via penetration through the epidermis of the host animal) systemically available in the host, as well as externally present on the host.

Another embodiment of the third aspect of the invention provides a pour-on formulation for control of Phthiraptera, Siphonaptera and Acarina pests in domestic animals, said formulation including:

(a) from 0.1 to 40% by weight of at least one active agent of the first aspect of the present invention, and (b) from 60-99.9% by weight of a suitable carrier selected from the group consisting of TPM/alcohol, OP/IPM/OSU and GTCC/PMP/CAP where TPM is Tripropylene glycol methyl ether;

P is octyl palmitate or 2-ethylhexyl palmitate which is an excellent lubricant, and can also be used as an emollient and a solvent;

P can be replaced by OS (octyl stearate or 2-ethylhexyl stearate);

PM is isopropyl myristate which has excellent spreading and emollient properties—this can be used interchangeably with IPP or IPL;

PP is isopropyl palmitate;

PL is isopropyl laurate;

MP is PPG 2 myristyl ether propionate which spreads rapidly and promotes wetting of other materials;

SU is di-2-ethylhexyl succinate and promotes wetting and spreading of lipophilic substances onto the skin;

CS is isocetyl stearate which can be used as an emollient, lubricant and spreading agent;

TCC is glyceryl tri caprylate/caprate which is an excellent carrier or vehicle for actives;

AP is a selected blend of branched chain esters which again acts as an emollient and spreading agent;

alcohol could be benzyl alcohol, propyl alcohol, diacetone alcohol or other suitable alcohol.

other possible carriers which can be used in the formulations of the present invention include organic and inorganic alcohols, including propylene glycol which is a common ivermectin carrier, ethanol, propyl alcohol, benzyl alcohol, glycols and also detergents.

Typically, the formulations of the third aspect of the present invention, can be in the form of a powder, cream, suspension, spray, emulsion, foam, paste, aerosol, ointment, salve or gel. More typically, the formulation is a solution, and typically water soluble.

Typically, formulations of the second, third, fifth or sixth aspects of the present invention can be effectively applied to domestic animals such as sheep, cattle, goats, camelids, pigs, dogs, cats, poultry and horses, other ruminants and monogastrics.

Typically, the bait formulations of the fourth aspect of the present invention will be directly administered to Phthiraptera, Siphonaptera or Acarina pests.

Typically a pour-on formulation of the third aspect of the present invention is applied by pouring in one or several lines or in a spot on the dorsal midline (back) or shoulder of a domestic animal. More typically, the pour-on formulation is applied by pouring along the back of the animal, following the spine. A pour-on formulation can also be applied to the animal by other conventional methods including wiping an impregnated material over at least a small area of the animal, by using commercially available applicators, by means of a syringe, by spraying or by using a spray race.

Typically, approximately about 0.1-2000 mg active composition/kg of animal bodyweight is an effective amount for topical application to domestic animals. Typically, about 2-100 mg of active composition of the first aspect of the present invention will be applied to a cow or sheep (per kg bodyweight).

Typically, a formulation of the present invention, such as a pour-on formulation, is formulated such that the active composition is present in a concentration of about 0.1-40% weight/volume, more typically 0.1-20% weight/volume, preferably about 0.5 to 5% depending on the potency of the active.

Typically, an active composition or a formulation of the present invention is formulated for use such that each of the A83543 compound and the macrocyclic lactone are present in a concentration range of about 1-500 ppm. More typically, each of the A83543 compound and the macrocyclic lactone are present in a concentration range of about 1-300 ppm. Even more typically, each of the A83543 compound and the macrocyclic lactone are present in a concentration range of about 1-100 ppm. The 1-500 ppm concentration is most typical in respect of ready to use formulations such as diluted dips and sprays. Pour-on formulations of the present invention will typically have a concentration of the actives in the range of from 1-100 g/L, more typically 5 to 50 g/L, even more typically 10-25 g/L. In respect of oral formulations, such as tablets and parenteral formulations of the present invention, typically the administered dose will be from 0.01 to 50 mg/kg animal body weight, more typically 0.1 to 20 mg/kg. For bait formulations of the present invention, it is typical that the concentration is from 0.05 to 1000 mg/kg, more typically 1 to 100 mg/kg.

Typically only a small volume of a pour-on formulation is required in order to be effective against the Phthiraptera, Siphonaptera and Acarina pests, such as in the order of 0.5-80 ml per application, with 10-60 ml per application being preferred for larger animals such as cattle and 1-20 ml per application for smaller animals such as sheep, dogs and cats.

Typically a formulation of the fifth aspect of the present invention is in the form of a tablet, capsule, bolus, solution, suspension or other elixir. The formulations can also be sustained release formulations. Such formulations are prepared in a conventional manner in accordance with standard pharmaceutical and veterinary practice. Typically, capsules, boluses or tablet may be prepared by admixture of the active combination with a suitable dinely divided diluent or carrier, additionally containing a disintegrant and/or a binder such as talc, starch or lactose.

Also typically, a formulation of the sixth aspect of the present invention is in the form of a sterile aqueous solution or suspension of the active combination, with a parenterally acceptable carrier being water and other excipents such as salt or glucose being optionally present.

In the formulations of the present invention having pesticidal activity against Phthiraptera, Siphonaptera and Acarina pests, the active agent is a combination of at least one compound selected from the class of spinosyn compounds (including spinosad) and at least one active agent selected from the macrocyclic lactones including ivermectin, abamectin, moxidectin, doramectin, eprinomectin and milbemycin.

The formulations of the present invention suitably can variously include one or more additional ingredients such as preservatives, spreading agents, adhesion promoters, active solubilisers such as oleic acid or lactic acid, viscosity modifiers, UV blockers or absorbers, colourants and stabilisers such as antioxidants. Suitably, surface active agents including anionic, cationic, non-ionic and ampholytic surface active agents can also be included in the pour-on formulations of the present invention.

Isopropyl myristate (IPM), isopropyl palmitate (IPP), caprylic/capric acid esters of saturated $C_{12}$-$C_{18}$ fatty alcohols, oleic acid, oleyl ester, ethyl oleate, triglycerides, silicone oils and dipropylene glycol mono methyl ether (DPM) are common spreading agents used in pour-on formulations.

Typically, the methods of the seventh to tenth aspects of the present invention prevent ticks, lice, fleas, and other Phthiraptera, Siphonaptera and Acarina pest infestations of domestic animals, including but not limited to cattle, sheep, goats, pigs, horses, camelids, dogs, cats and poultry and other ruminants and monogastrics.

Typically, the active compositions, formulations and methods of the present invention are effective against immature (including nymph) and adult forms of Phthiraptera, Siphonaptera and Acarina pests. The pests do not have to be, although typically are present on a host domestic animal.

More typically, the active compositions, formulations and methods of the present invention are effective against immature and adult forms of Phthiraptera, Siphonaptera and Acarina pests in domestic animals. Also typically, the active compositions, formulations and methods of the present invention are also effective in decreasing the number of viable Phthiraptera, Siphonaptera and Acarina eggs which may be present in domestic animals.

More typically, a topically, orally or parenterally administered formulation of the present invention acts to control sheep body lice (*Bovicola Ovis*) in sheep, acts to control similar lice in cattle, goats and camelids, acts to control ticks (eg *Boophilus bovis*), on cattle and acts to control Siphonaptera (*Ctenocephalides felis* and other fleas) in dogs, cats and other domestic animals. Also more typically, a topically, orally or parenterally administered formulation of the present invention acts to control lice and ticks in cattle and fleas in both dogs and cats.

The formulations of the present invention are prepared according to known techniques. Where the formulation is a solution the parasiticide/insecticide is mixed with the carrier or vehicle, using heat and stirring where required. Auxiliary or additional ingredients can be added to the mixture of active and carrier or can be mixed with the active prior to the addition of the carrier.

The formulations of the present invention can contain as little as 1 ppm of each macrocyclic lactone compound and spinosyn compound per application and a synergistic effect is still observed.

The active compositions and formulations of the invention are non toxic to humans and animals as well as crops and plants, and residues in the wool, hides and tissue of animals treated or administered with the formulations are at environmentally acceptable levels. Further no skin irritation or other toxicity to end users results from the method and formulations of this invention. Environmental contamination is also minimised.

Also advantageously, as such spinosyn factors and macrocyclic lactones are very efficacious at low levels due to their synergistic effect when combined together, the present invention is of utility against Phthiraptera, Siphonaptera and Acarina pest populations in domestic animals that have existing levels of resistance to both spinosyn compounds and macrocyclic lactones when these compounds are used separately.

Generally the administration of the formulations of the third aspect of the present invention, and active compositions of the present invention is by way of externally/topically to the domestic animals. Such topical application can take the form of dipping, showering, jetting, spraying, manually applying such as dusting, or otherwise placing or laying the formulation containing the active substance/s. Accordingly, typically the active compositions of the invention are formulated into a number of topically applied pesticidal formulations.

Preferably such topical pesticidal formulations include spot-ons, pour ons, sprays, dips, dusts, lotions, gels, ointments, salves, dressings, towels, cremes, sticks, soaps, shampoos, collars, medallions, eartags and tail bands. Pour-on formulations including both aqueous and organic solvent based ones as well as emulsions and suspensions are preferred. As stated above, the formulations can be in a concentrated form which are diluted just prior to application.

More preferred are dip formulations, pour on formulations, jetting fluid formulations and jetting/spray race formulations.

Wettable powders are another formulation of the invention which are prepared by blending the active with a dust carrier which wets and suspends in water. A surface active agent can be added. Sprays of wettable powders can be applied to the environs of domestic animals including poultry houses, stables, dairy sheds and pig pens because of their relative safety.

Emulsions are another formulation of the invention which are solutions of the active in water-immiscible organic solvents, commonly at 1-40%, with an optional surface active agent to promote emulsification, wetting and spreading. The choice of solvent is based on safety to plants, humans and animals, volatility, flammability and cost. Water emulsion sprays from such emulsion concentrates can be used in household Phthiraptera, Siphonaptera and Acarina pest control.

As stated above, the administration of the formulations of the fifth aspect of the present invention is by way of oral administration while the administration of the formulations of the sixth aspect of the present invention is parenterally, for example intramuscularly, subcutaneously or intravenously.

The formulations of the fifth and sixth aspects of the present invention will vary with regard to the weight of the active combination depending of the species of host domestic animal to be treated as well as the body weight. The formulations may be administered as a dose of from 0.001 mg to about 50 mg per kg of animal body weight, more typically from 0.01 to about 30 mg per kg of animal body weight, and even more typically from 0.1 to about 20 mg per kg of animal body weight. This can be given as a single dose or as several doses. Higher as well as lower dosage ranges are also contemplated within the present invention As the administration of the bait formulations of the fourth aspect of the present invention is by way of directly to the pest and not to a host domestic animal, administration occurs by way of ingestion of the bait by the pest.

The spinosyn component of the active composition of the first aspect of the present invention may be present as a single compound, a mixture of two or more compounds, a mixture including at least one of A83543A and A83543D, or a mixture of at least one A83543 compound together with the dried portion of the fermentation medium in which it is produced.

The macrocyclic lactone compounds used in the present invention include such well known anthelmintic compounds as avermectins and milbemycins and derivatives and analogues thereof. As stated above, the avermectins are isolated from fermentation products of *Streptomyces avermitilis* and the isolation and chemical structure of the eight individual acomponents which make up the avermectins (otherwise known as C-076 compounds) is described in detail in British patent specification 1573995. Ivermectin is a compound which is a semisynthetic chemical formed by modification of avermectin. Commercially available ivermectin can include for example, the 25-isopropyl analogue of ivermectin. Avermectins being lipophilic can be prepared for the purposes of the formulations and methods of the present invention by dissolving an avermectin in an organic solvent such as chloroform, methylene chloride, acetone and alcohols. Milbemycins as discussed above in detail, are other compounds which are not avermectins but which can be considered to come within the class of compounds which are macrocyclic lactones. The milbemycins differ structurally from the avermectin group, mainly in the absence of a disaccharide group on C-13. Examples of such compounds are described in UK patent 1390336 and EP patent applications 170006, 254583, 334484 and 410615 which are incorporated herein by cross reference.

The spinosyn compound may also be present as a salt in the active agent, formulations and methods of this invention. The salts would be prepared using standard procedures for salt preparation. For example, spinosyn A can be neutralised with an appropriate acid to form an acid additional salt. The acid addition salts of spinosyns which can be used in the present invention are useful and include salts formed by reaction with either an organic or inorganic acid such as, for example, sulfuric, hydrochloric, phosphoric, acetic, succinic, citric, lactic, maleic, fumaric, cholic, pamoic, mucic, glutamic, camphoric, glutaric, glycolic, phthalic, tartaric, formic, lauric, stearic, salicyclic, methanesulfonic, benzenesulfonic, sorbic, picric, benzoic, cinnamic and other like acids.

Generally, emulsifiable concentrates of the A83543 compounds comprise a convenient concentration of an A83543 compound dissolved in an inert carrier which is either a water-miscible solvent or a mixture of a water immiscible organic solvent and emulsifiers. A preferred concentration range is 1-500 g/L of said spinosyn compound, more preferably the concentration range is selected from the group consisting of 1-400 g/L, 1-350 g/L, 1-300 g/L, 1-250 g/L, 1-200 g/L, 1-150 g/L, 1-100 g/L, 1-90 g/L, 1-80 g/L, 1-70 g/L, 1-60 g/L, 1-50 g/L, 1-40 g/L, 1-30 g/L, 1-20 g/L, even more preferably 25 g/L. Useful organic solvents include aromatics including xylenes and petroleum fractions. Other organic solvents may also be used, such as the terpenic solvents, including rosin derivatives, aliphatic ketones such as cyclohexanone and complex alcohols such as 2-ethoxyethanol.

Suitable emulsifiers for emulsifiable concentrates can be chosen from conventional nonionic surfactants, including ethylene oxide adducts of alkylphenols and anionic surfactants, including sulphonate alkyl/aryl salts.

Aqueous suspensions (AS) comprise suspensions of an active water-insoluble spinosyn compound dispersed in an aqueous vehicle at a concentration in the range of from about 1-500 g/L, preferably the concentration range is selected from the group consisting of about 1-400 g/L, about 1-300 g/L, about 1-250 g/L, about 1-200 g/L about 1-150 g/L, about 1-100 g/L, about 1-50 g/L, about 1-45 g/L, about 1-40 g/L, about 1-30 g/L, more preferably about 25 g/L. Generally the suspensions are prepared by finely grinding the spinosyn compound and mixing it into a vehicle comprised of water and surfactants chosen from such types as nonionic, sulfonated lignins and alkylsulfates. Inert ingredients may also be added.

The aqueous suspensions and emulsions are preferably diluted with water to obtain the desired spinosyn concentration in the final formulations of the invention. In another preferred formulation, the one or more active substances take/s the form of a solution of the active/s in water. Sprays are the most common means of pesticide application on surfaces of structures such as stables, dairy sheds and pig pens. Sprays or dips are the most common means of pesticide application on small ruminant animal species with water generally as the principal carrier.

In the formulations of the present invention, particularly dip wash formulations it is preferred that the spinosyn compound and the macrocyclic lactone compound are each present in a concentration of about 500 ppm or less. More typically, each are present in a concentration of about 400 ppm or less. Also typically, each are present in a concentration of about 300 ppm or less, more typically 200 ppm or less, even more typically 100 ppm or less, most typically 50 ppm or less.

BEST MODE AND OTHER MODES OF PERFORMING THE INVENTION

Preparation of the preferred formulations of the present invention can be made by conventional processes, several examples of which are found below. The preferred process for preparing a spinosad and ivermectin combination of the present invention is to either co-formulate the combination or formulate each of the compounds separately then combine them together. The compounds could even exist in the combination as separate phases. For example, one active compound of the synergistic composition could be in solution with the other active compound being in suspension; such a combination then being used to prepare a suitable formulation of the present invention.

EXAMPLES

Introduction

Synergy (or co-potentiation) occurs when the combined effect of two pesticides is significantly greater than the additive effect of each individually at the concentrations tested. For example, the method of Sun and Johnson (1960) "Analysis of joint action of insecticides against house flies" *J. Econ. Entomol* 53:887-892, requires the calculation of co-toxicity coefficients. Co-toxicity coefficients of 100 indicate additive action only whereas of 130 or higher indicate synergy or potentiation. Alternatively a generalised linear model approach can be employed to generate dose-response lines for each chemical. The lines for each separate chemical are used to predict the efficacy of the combinations assuming independent action, ie no synergism or potentiation. The predicted lines are compared with the observed effect of the combinations and significant potentiation can be detected.

The macrocyclic lactones have a primary effect on the insect nervous system by activating inhibitory glutamate receptors, while spinosyns primarily activate the nicotinic acetylcholine receptors in insect neurones causing hyperactivity of neurones. However, both spinosyns and macrocyclic lactones have a secondary effect on gamma aminobutyric acid (GABA) gated chloride channels in arthropod neurones, GABA being an inhibitory neuro-transmitter. It is therefore possible that when combined spinosyns and macrocyclic lactones have a synergistic effect on the GABA receptor leading to effects in an insect's nervous system which would be unrelated to the primary effect of either spinosyns or macrocyclic lactones. The aim of these studies was to test the hypothesis in Phthiraptera, Siphonaptera and Acarina pests of veterinary importance.

The following examples illustrate the surprising result that synergy occurs when a spinosyn and a macrocyclic lactone are given together to an animal pest in such a way that the chemicals are ingested or present systemically in the pest. Surprisingly, this effect is not observed in in vitro assays which rely on contact such as treated paper or transient immersion in treated solutions. It is contemplated that this difference is related to the mechanisms of action and the nature of both chemicals which have low vapour pressure and do not readily cross the cuticle of arthropods.

Example 1

In-Vitro Assays to Investigate Possible Synergism Between Spinosad and Ivermectin on Lice Materials and Methods Using the methods of Rugg and Thompson (*J Aust Ent Soc*, 1993; 32:1-3) groups of 4×15 lice are allowed to feed on ground sheep epidermis containing a range of concentrations of spinosad or ivermectin for 48 hour. Mortality is assessed after 48 hours and LC90 values determined by probit analysis. Lice are exposed to the LC90 concentration of spinosad or ivermectin and ½, ¼ and ⅛ of the LC90. In addition lice are exposed to 1:1, 1:4, 4:1, 9:1 and 1:9 combinations of each chemical with each concentration of chemical being a fraction of the LC90.

The method of generalized linear models for overdispersed binomial data using the logistic link function is used for an analysis of the treatment groups. The analysis estimates dose-response lines (on the logarithmic dose scale) for each chemical or combination. The dose response lines are used to predict the efficacy of the combinations assuming independent action and compared with the efficacy observed.

Results

There is significant potentiation in most of the combinations tested. Potentiation is most pronounced using 4:1 and 9:1 ratios of spinosad:ivermectin.

Comparative Example

Paper Contact Assay in Respect of Lice

Materials and Methods

Groups of 4×10-13 lice are exposed to a range of concentrations of spinosad or ivermectin on cotton squares in petri dishes. Mortality is assessed after 18 hours and LC90 values are determined by probit analysis. Lice are exposed to the LC90 concentration of spinosad or ivermectin and ½, ¼ and ⅛ of the LC90. In addition lice are exposed to 1:1, 1:4, 4:1, 9:1 and 1:9 combinations of each chemical with each concentration of chemical being a fraction of the LC90.

Results

All efficacy estimates for the combinations in groups are less than those predicted under independent action, i.e. there is no evidence of synergism.

Discussion

The negative result in the paper contact assay compared to the ingestion assay supports the hypothesis that both chemicals must be presented systemically to the pest for potentiation to occur.

Example 2

In Vitro Assays to Investigate Synergism Between Spinosad and Ivermectin in Fleas I) Artificial Membrane System for Adult Fleas.

Materials and Methods

The artificial membrane system (artificial dog) devised by Wade and Georgi (*J Med Entomol* 1988; 25:186-190) allows adult fleas to feed on blood and is suitable to detect the effect of systemic insecticides. Groups of 25 fleas are allowed to feed on citrated blood containing a range of concentrations of spinosad or ivermectin for 24 hours. Mortality is assessed after 24 hours and LC90 values determined by probit analysis. Fleas are exposed to the LC90 concentration of spinosad or ivermectin and ½, ¼ and ⅛ of the LC90. In addition fleas are exposed to 1:1, 1:4, 4:1, 9:1 and 1:9 combinations of each chemical with each concentration of chemical being a fraction of the LC90.

Results

There is significant potentiation in most of the combinations tested. Potentiation is most pronounced using 4:1 and 9:1 ratios of spinosad:ivermectin.

II) Flea Larvae Feeding Study

Materials and Methods

The methods of El-Gazzar et al (*J Med Entomol* 1986; 23:651-654) are used. Groups of 50 flea larvae are allowed to feed on larval rearing medium containing a range of concentrations of spinosad or ivermectin for 4 weeks. After 4 weeks the number of live emerged adults, cocoons and dead pupae are counted. Larval mortality is assessed and LC90 values determined by probit analysis. Larvae are exposed to the LC90 concentration of spinosad or ivermectin and ½, ¼ and ⅛ of the LC90. In addition larvae are exposed to 1:1, 1:4, 4:1, 9:1 and 1:9 combinations of each chemical with each concentration of chemical being a fraction of the LC90.

Results

There is significant potentiation in most of the combinations tested.

Example 3

In Vitro Assays to Investigate Synergism Between Spinosad and Ivermectin in Cattle Ticks I) Larval Immersion Studies.

Materials and Methods

The larval immersion test described by Sabatini, Kemp and others (*Vet Parasitol* 2001; 95:53-62) is used except that larvae are desiccated for 12 hours first to induce them to imbibe the immersion liquid when immersed. Groups of 500 larvae are immersed in liquids containing a range of concentrations of spinosad or ivermectin in for 20 minutes then transferred to paper packets. Mortality is assessed after 24 hours and LC90 values determined by probit analysis. Tick larvae are exposed to the LC90 concentration of spinosad or ivermectin and ½, ¼ and ⅛ of the LC90. In addition larvae are exposed to 1:1, 1:4, 4:1, 9:1 and 1:9 combinations of each chemical with each concentration of chemical being a fraction of the LC90.

Results

There is significant potentiation in most of the combinations tested. Potentiation is most pronounced using 4:1 and 9:1 ratios of spinosad:ivermectin.

II) Adult Injection Study.

Materials and Methods

Adult engorged ticks are injected with 2 microliters of a range of concentrations of spinosad or ivermectin. Egg laying and larval hatch data are collected according to standard methods—for example Sabatini and Kemp (*Vet Parasitol* 2001; 95:53-620) and used to calculate LC90 values. Adults are injected with the LC90 concentration of spinosad or ivermectin and ½, ¼ and ⅛ of the LC90. In addition adults are injected with 1:1, 1:4, 4:1, 9:1 and 1:9 combinations of each chemical with each concentration of chemical being a fraction of the LC90.

Results

There is significant potentiation in most of the combinations tested, especially the 4:1 and 9:1 spinosad:ivermectin ratios.

Comparative Example

Tick Larval Immersion without Imbibing of Immersion Fluid

The larval immersion test described by Sabatini, Kemp and others (*Vet Parasitol* 2001; 95:53-62) is used. Groups of 500 larvae are immersed in liquids containing a range of concentrations of spinosad or ivermectin for 20 minutes then transferred to paper packets. Mortality following immersion is assessed after 24 hours and LC90 values determined by probit analysis. Tick larvae are exposed to the LC90 concentration of spinosad or ivermectin and ½, ¼ and ⅛ of the LC90. In addition larvae are exposed to 1:1, 1:4, 4:1, 9:1 and 1:9 combinations of each chemical with each concentration of chemical being a fraction of the LC90.

Results

A dose response relationship is observed for both compounds. Efficacy estimates for the combinations are less than those predicted under independent action i.e. there is no evidence of potentiation.

Discussion

The negative results for potentiation in the assay where imbibing of test medium does not occur compared to the positive evidence of potentiation where larvae imbibe test medium supports the hypothesis that both chemicals must be presented systemically to the ticks for potentiation to occur.

Examples of Spinosad Ivermectin Synergistic Formulations to Control Phthiraptera, Siphonaptera and Acarina Pests Example 4

Pour-On Formulation

| Ingredients | g/L |
| --- | --- |
| Spinosad | 20 |
| Ivermectin | 5 |
| antioxidant such as BHT | 0.5 |
| Crodamol IPM | 15 |
| Crodamol OSU | 15 |
| Crodamol OP | to 100% |

The formulation is applied to the dorsal midline of animals from the poll to the base of the tail using an applicator, usually a self filling dosing gun with a nozzle to dispense a narrow or wide band or lines of formulation along the back. The formulation is applied at 0.2 mL per kilogram body weight. Alternatively a set volume is applied to each bodyweight class—eg for sheep 10 mL for animals less than 30 kg, 15 for animals 31-50 kg and 20 ml for animals 51+kg. Sheep and other fibre producing animals should be treated within 24 hours of shearing or fibre collection.

Example 5

Suspension Concentrate, 20 g/L Spinosad, 5 g/L Ivermectin

The active chemicals are ground into fine particles using a bead mill.

| | % w/w |
| --- | --- |
| Spinosad | 2 |
| Ivermectin | 0.5 |
| Propylene glycol | 10 |
| Surfactant eg Pluronic P123 | 2 |
| Mineral thickener eg Veegum | 2 |
| Xanthum gum eg Rhodopol 23 | 0.2 |
| Antimicrobial eg Agent Dowicil 75 | 0.2 |
| Antifoam Agent eg Antifoam C | 0.1 |
| Water deionised | to 100% |

The suspension concentrate (SC) is diluted 1:1000 in water and used to fill a bath or dip. The chemical is applied to animals by immersing them. Alternatively a shower dip or jetting race can be used to wet animals to the skin. Sheep can be treated by using a hand jetting wand to pump the diluted chemicals into the wool. For wound dressings the diluted chemicals can be poured into a wound. A number of animal species can be treated by being sprayed with diluted product to control Phthiraptera, Siphonaptera and Acarina pests that plague domestic animals.

Example 6

Emulsifiable Concentrate 20 g/L Spinosad, 5 g/L Ivermectin

The active chemicals are ground into fine particles using a bead mill.

| | % w/w |
| --- | --- |
| Spinosad | 2 |
| Ivermectin | 0.5 |
| Antioxidant eg BHT | 0.5 |
| 10% of a blend of ionic and non ionic surfactants For example Toximul 3453F | 6.8 |
| Toximul 3454FA | 3.2 |
| Aromatic hydrocarbon solvent For example Solvesso 150 to give | 100% |

The emulsifiable concentrate (EC) is diluted 1:1000 in water and used to fill a bath or dip. The chemical is applied to animals by immersing them. Alternatively a shower dip or jetting race can be used to wet animals to the skin. Sheep can be treated by using a hand jetting wand to pump the diluted chemicals into the wool. For wound dressings the diluted chemicals can be poured into a wound. A number of animal species can be treated by being sprayed with diluted product to control Phthiraptera, Siphonaptera and Acarina pests that plague domestic animals.

Example 7

Oral tablet formulation for dogs for a 20 kg dog, 500 mg tablet.

| Ingredients | g/kg |
|---|---|
| Core tablet | |
| Spinosad | 400 |
| Ivermectin | 40 |
| Binding agent eg Povidone | 24 |
| Binder/disintegrating agent, eg Sodium starch glycollate | 20 |
| Lubricant eg Magnesium stearate | 7 |
| Coating | |
| Film forming agent Hydroxypropyl methylcellulose | 25 |
| Plasticiser eg glycerin | 4 |
| Colour agent | 20 |

Example 8

Injection Formulation

| Ingredients | g/L |
|---|---|
| Spinosad | 100 |
| Ivermectin | 20 |
| Solvent eg propylene glycol | 350 |
| Solvent eg glycerol formol | 500 |
| Preservative | 0.1 |
| Antioxidant | 0.1 |

Example 9

Bait Formulation

| Ingredient | g/kg |
|---|---|
| Spinosad | 0.1 |
| Ivermectin | 0.05 |
| Ground dried bovine blood | 100 |
| Ground dried dog food | 400 |
| Yeast | 1 |
| Preservative | 0.01 |
| Vermiculite | 500 |

The invention claimed is:

1. A systemically active oral composition for controlling fleas in dogs comprising a combination of spinosad, or a salt thereof, and milbemycin oxime in a 10:1 to 100:1 weight/weight ratio, and wherein said flea is *Ctenocephalides felis*.

2. The composition of claim 1 wherein said spinosad or salt thereof and milbemycin oxime are from 0.1%-40% by weight of the composition.

3. The composition of claim 2 wherein from 60-99.9% by weight of the composition is at least one veterinarily acceptable carrier, diluent, or excipient.

4. The composition of claim 1 wherein said composition is in the form of a tablet, capsule, bolus, solution, suspension, or elixir.

5. The composition of claim 1 wherein said composition comprises spinosad.

6. The composition of claim 3 wherein said composition comprises spinosad.

7. A method of controlling *Ctenocephalides felis* in a dog comprising administering an effective amount of a systemically active oral composition comprising a combination of spinosad, or a salt thereof, and milbemycin oxime in a 10:1 to 100:1 weight/weight ratio, to said dog.

8. The method of claim 7 wherein said spinosad, or a salt thereof, and milbemycin oxime are from 0.1%-40% by weight of the composition.

9. The method of claim 8 wherein from 60-99.9% by weight of the composition is at least one veterinarily acceptable carrier, diluent, or excipient.

10. The method of claim 7 wherein said composition is in the form of a tablet, capsule, bolus, solution, suspension, or elixir.

11. The method of claim 7 wherein said composition comprises spinosad.

12. The method of claim 9 wherein said composition comprises spinosad.

13. The method of claim 12 wherein said composition is in the form of a tablet, capsule, bolus, solution, suspension, or elixir.

14. The method of claim 13 wherein said composition is in the form of a tablet.

* * * * *